(12) United States Patent
Young et al.

(10) Patent No.: US 9,175,333 B2
(45) Date of Patent: Nov. 3, 2015

(54) CAPS FOR SAMPLE WELLS AND MICROCARDS FOR BIOLOGICAL MATERIALS

(71) Applicant: APPLIED BIOSYSTEMS, LLC, Carlsbad, CA (US)

(72) Inventors: Eugene Young, Marietta, GA (US); Steven Boege, San Mateo, CA (US); Donald Sandell, San Jose, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

(21) Appl. No.: 14/088,230

(22) Filed: Nov. 22, 2013

(65) Prior Publication Data

US 2014/0248691 A1 Sep. 4, 2014

Related U.S. Application Data

(60) Continuation of application No. 12/099,644, filed on Apr. 8, 2008, now Pat. No. 8,591,836, which is a division of application No. 10/602,113, filed on Jun. 23, 2003, now abandoned.

(51) Int. Cl.
| | |
|---|---|
| *B01L 9/00* | (2006.01) |
| *C12Q 1/68* | (2006.01) |
| *B01L 3/00* | (2006.01) |
| *G01N 21/03* | (2006.01) |

(52) U.S. Cl.
CPC ............ *C12Q 1/6806* (2013.01); *B01L 3/50825* (2013.01); *B01L 3/50853* (2013.01); *G01N 21/0303* (2013.01); *B01L 2300/042* (2013.01); *B01L 2300/046* (2013.01); *B01L 2300/0654* (2013.01); *B01L 2300/0851* (2013.01)

(58) Field of Classification Search
USPC .................................................. 422/568, 569
See application file for complete search history.

(56) References Cited

U.S. PATENT DOCUMENTS

| | | | |
|---|---|---|---|
| 2,961,108 | A | 10/1960 | Johnson |
| 3,932,132 | A | 1/1976 | Hijikata |
| 4,044,889 | A | 8/1977 | Orentreich et al. |
| 4,516,856 | A | 5/1985 | Popelka |
| 4,560,269 | A | 12/1985 | Baldszun et al. |

(Continued)

FOREIGN PATENT DOCUMENTS

| | | |
|---|---|---|
| AT | 00400638 | 2/1996 |
| DE | 04405375 | 8/1995 |

(Continued)

OTHER PUBLICATIONS

EP 06 02 5970, European Search Report for Application No. EP 06 02 5970 dated Feb. 5, 2007, along with opinion on patentability by the Search Division., Feb. 5, 2007, 6 pages.

(Continued)

*Primary Examiner* — Paul Hyun

(57) ABSTRACT

A cover for a biological sample well tray, comprising a cap for sealing a sample well. The cap comprises a well lens for focusing light into the sample well and collecting light from the sample. In another aspect, the cap comprises an elongate portion configured to permit incoming light to pass into the sample well and out of the sample well. Various other aspects comprise a microcard for biological material, and an apparatus for a plurality of sample well strips. A method for testing a biological sample is also provided.

8 Claims, 11 Drawing Sheets

(56) References Cited

U.S. PATENT DOCUMENTS

| | | | |
|---|---|---|---|
| 4,566,791 A | 1/1986 | Goldsmith | |
| 4,577,970 A | 3/1986 | Meserol | |
| 4,599,315 A | 7/1986 | Terasaki et al. | |
| 4,619,530 A | 10/1986 | Meserol et al. | |
| 4,722,598 A | 2/1988 | Ford | |
| 4,787,722 A | 11/1988 | Claytor | |
| 4,873,993 A | 10/1989 | Meserol et al. | |
| 4,956,150 A | 9/1990 | Henry | |
| 4,999,303 A | 3/1991 | Jaeger et al. | |
| 5,038,852 A | 8/1991 | Johnson et al. | |
| 5,083,223 A | 1/1992 | Igarashi | |
| 5,100,238 A | 3/1992 | Nailor et al. | |
| 5,167,929 A * | 12/1992 | Korf et al. | 422/534 |
| 5,169,601 A | 12/1992 | Ohta et al. | |
| 5,210,038 A | 5/1993 | Jaeger et al. | |
| 5,319,436 A | 6/1994 | Manns | |
| 5,333,675 A | 8/1994 | Mullis et al. | |
| 5,342,581 A | 8/1994 | Sanadi | |
| 5,346,672 A | 9/1994 | Stapleton et al. | |
| 5,355,215 A | 10/1994 | Schroeder et al. | |
| 5,457,527 A | 10/1995 | Manns et al. | |
| 5,475,610 A | 12/1995 | Atwood et al. | |
| 5,487,872 A | 1/1996 | Hafeman et al. | |
| 5,599,503 A | 2/1997 | Manz et al. | |
| 5,656,493 A | 8/1997 | Mullis et al. | |
| 5,657,166 A | 8/1997 | Otaki | |
| 5,683,659 A | 11/1997 | Hovatter | |
| 5,722,553 A | 3/1998 | Hovatter | |
| 5,760,975 A | 6/1998 | DiGiovanni | |
| 5,863,791 A | 1/1999 | Baldszun et al. | |
| 5,910,287 A | 6/1999 | Cassin et al. | |
| 5,928,907 A | 7/1999 | Woudenberg et al. | |
| 5,928,935 A | 7/1999 | Reuss, Jr. et al. | |
| 5,958,349 A * | 9/1999 | Petersen et al. | 422/198 |
| 6,007,778 A | 12/1999 | Cholewa | |
| 6,015,674 A | 1/2000 | Woudenberg et al. | |
| 6,027,694 A | 2/2000 | Boulton et al. | |
| 6,040,171 A | 3/2000 | Ho et al. | |
| 6,042,789 A | 3/2000 | Antonenko et al. | |
| 6,066,245 A | 5/2000 | Trost | |
| 6,100,541 A | 8/2000 | Nagle | |
| 6,143,248 A | 11/2000 | Kellog et al. | |
| 6,159,368 A | 12/2000 | Moring et al. | |
| 6,171,780 B1 | 1/2001 | Pham et al. | |
| 6,193,088 B1 | 2/2001 | Vincent et al. | |
| 6,199,710 B1 | 3/2001 | Jensen | |
| 6,214,246 B1 | 4/2001 | Craighead | |
| 6,229,603 B1 | 5/2001 | Coassin et al. | |
| 6,238,911 B1 | 5/2001 | Kasahara | |
| 6,239,871 B1 | 5/2001 | Gilby | |
| 6,272,939 B1 | 8/2001 | Frye et al. | |
| 6,278,545 B1 | 8/2001 | Napier | |
| 6,340,589 B1 | 1/2002 | Turner et al. | |
| 6,383,820 B1 | 5/2002 | Bunn et al. | |
| 6,436,350 B1 | 8/2002 | Stanchfield et al. | |
| 6,503,456 B1 | 1/2003 | Knebel | |
| 6,514,464 B1 | 2/2003 | Knebel | |
| 6,767,607 B2 * | 7/2004 | Tanner et al. | 428/131 |
| 6,896,848 B1 | 5/2005 | Warhurst et al. | |
| 7,037,580 B2 | 5/2006 | Razavi et al. | |
| 2002/0001848 A1 | 1/2002 | Bedingham et al. | |
| 2002/0047003 A1 | 4/2002 | Bedingham et al. | |
| 2002/0048533 A1 | 4/2002 | Harms et al. | |
| 2002/0064885 A1 | 5/2002 | Bedingham et al. | |
| 2002/0092767 A1 | 7/2002 | Bjornson et al. | |
| 2002/0092973 A1 | 7/2002 | Nagle | |
| 2003/0034306 A1 | 2/2003 | Schulte et al. | |
| 2003/0039592 A1 | 2/2003 | Knebel | |
| 2003/0152942 A1 * | 8/2003 | Fors et al. | 435/6 |
| 2003/0235519 A1 | 12/2003 | Sha et al. | |
| 2008/0194014 A1 | 8/2008 | Young et al. | |

FOREIGN PATENT DOCUMENTS

| | | |
|---|---|---|
| DE | 19739119 | 3/1999 |
| EP | 0065409 | 11/1982 |
| EP | 0545284 | 6/1993 |
| EP | 0545673 | 6/1993 |
| EP | 0606534 | 7/1994 |
| EP | 0895240 | 2/1999 |
| EP | 0955097 | 11/1999 |
| EP | 1088590 | 4/2001 |
| JP | 2003-04629 | 1/2003 |
| WO | WO-8607288 | 12/1986 |
| WO | WO-9117239 | 11/1991 |
| WO | WO-9736681 | 10/1997 |
| WO | WO-0115807 | 3/2001 |
| WO | WO-0128684 | 4/2001 |
| WO | WO-0200347 | 1/2002 |
| WO | WO-0201180 | 1/2002 |
| WO | WO-0201181 | 1/2002 |
| WO | WO-02087763 | 11/2002 |

OTHER PUBLICATIONS

PCT/US2004/020335, Annex to Form PCT/rSA/206 communication Relating to the Results of the Partial International Search for International Application No. PCT/US2004/020335, Dec. 14, 2004, 5 pages.

Andreas, Gerlach, "Glass Bottom Microplates (24, 96, 384, 1536 Well) for High Performance Detection, 2. BioSensor Symposium Tuebingen", http://Barolo.ioc.uni-tuebingen.de/biosensor2001, 2001, 2 pgs.

* cited by examiner

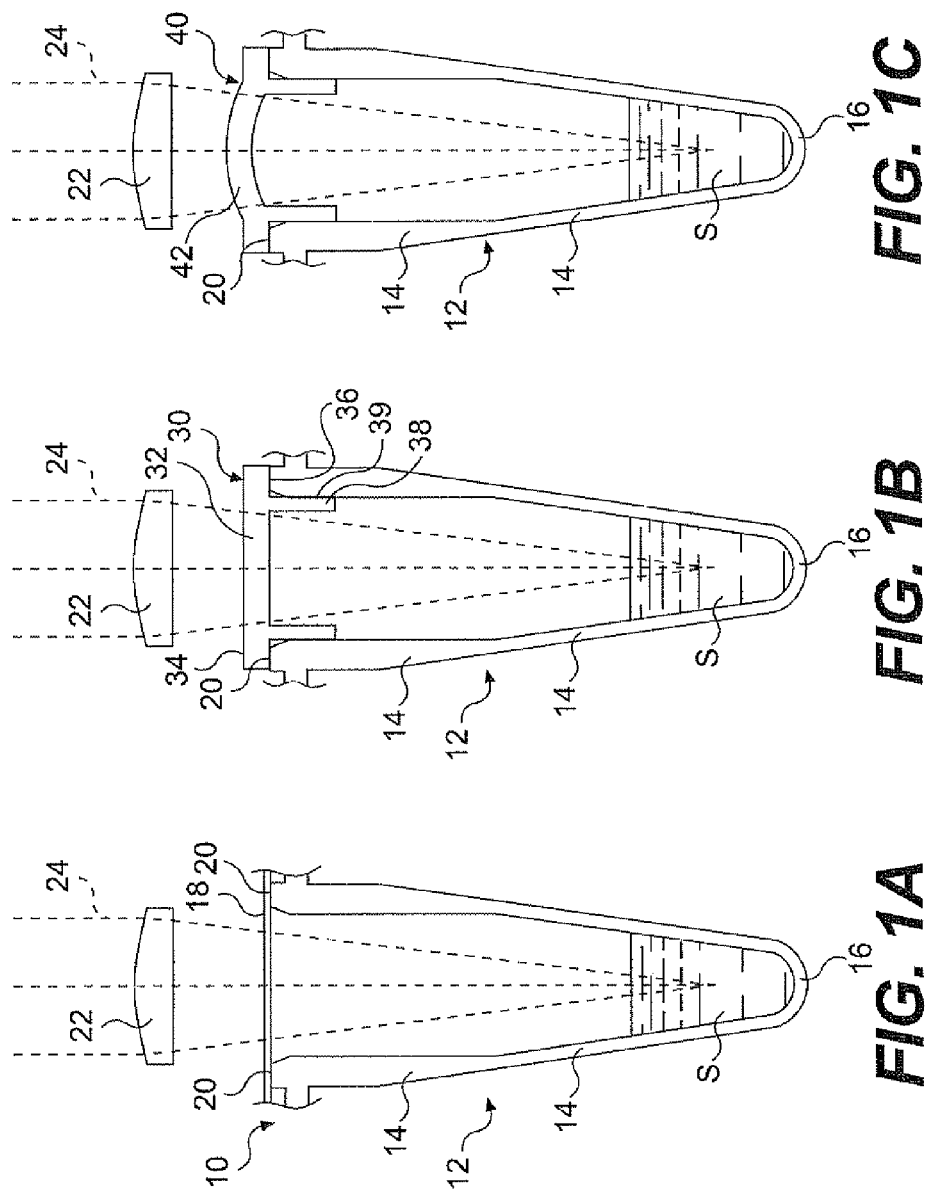

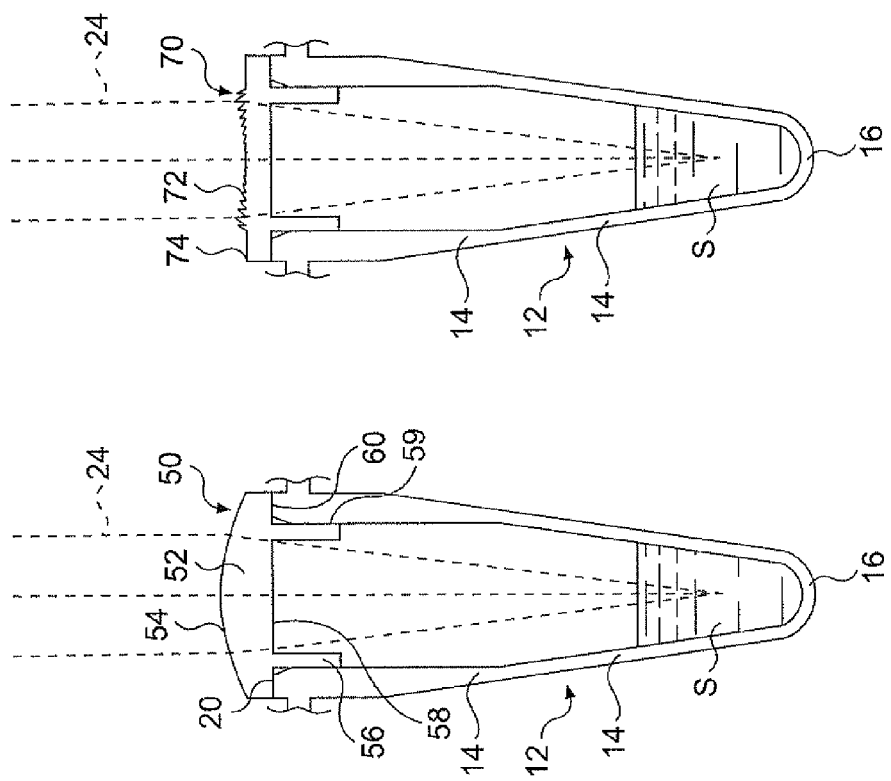

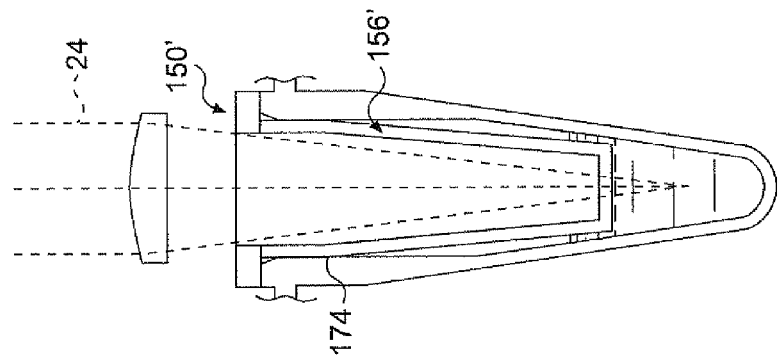
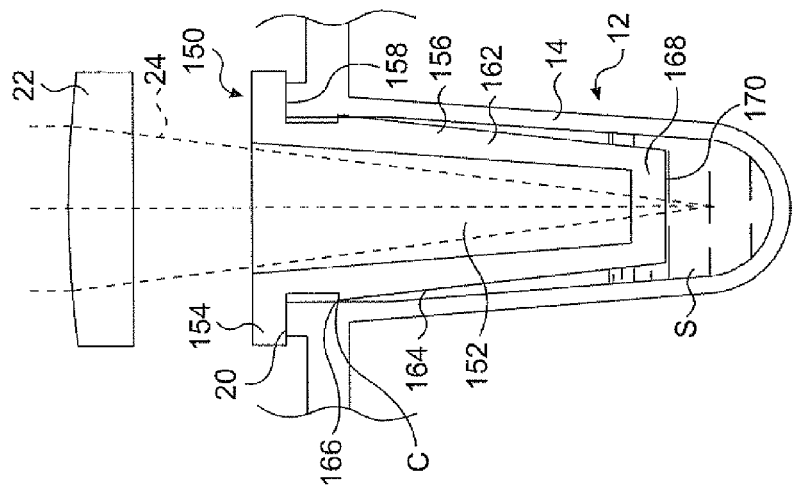
FIG. 6A
FIG. 6B

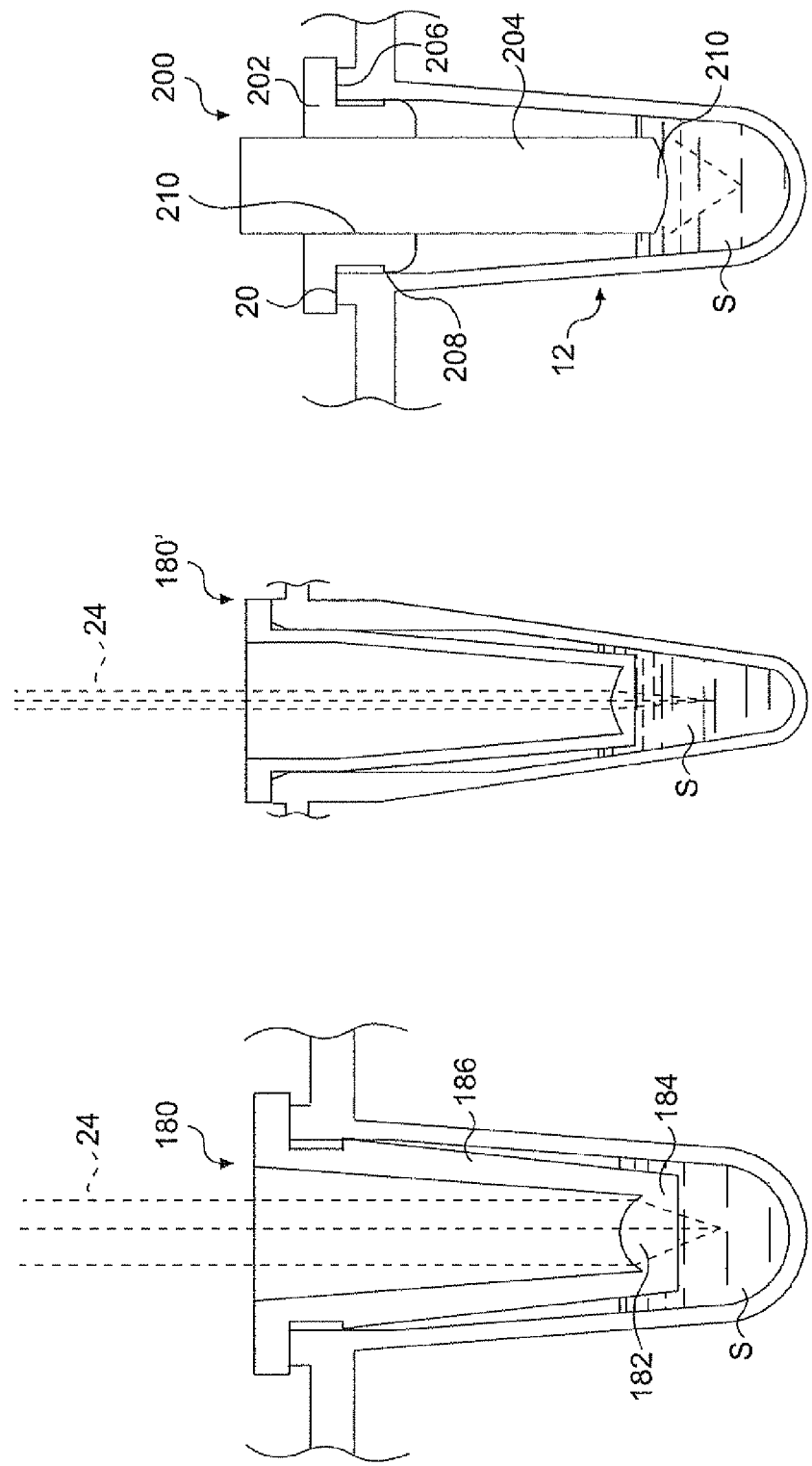

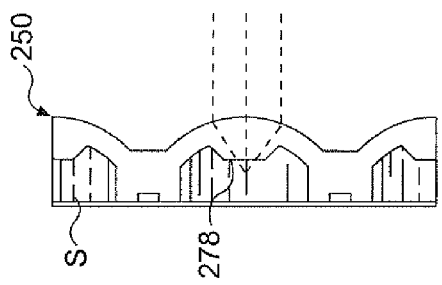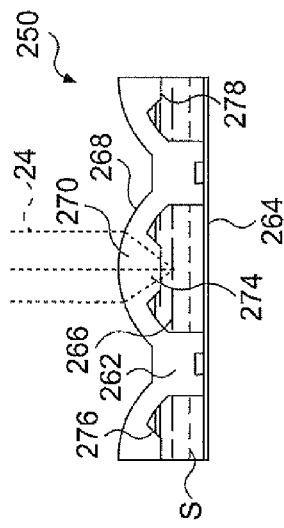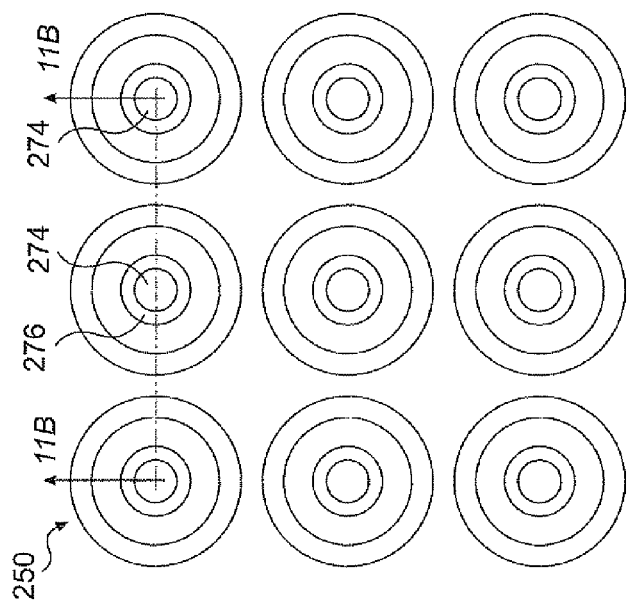

CAPS FOR SAMPLE WELLS AND MICROCARDS FOR BIOLOGICAL MATERIALS

CROSS-REFERENCE TO RELATED APPLICATIONS

This application is a continuation of U.S. application Ser. No. 12/099,644, filed Apr. 8, 2008, which is a division of U.S. application Ser. No. 10/602,113, filed Jun. 23, 2003, which disclosures are herein incorporated by reference in their entirety.

FIELD

The present teachings relate to devices and methods for containing samples of biological material. The present teachings relate to well lenses for the samples of biological material that can be contained in a sample container.

BACKGROUND

Biological testing has become an important tool in detecting and monitoring diseases. In the biological testing field, polymerase chain reactions (PCR), ligase chain reactions, antibody binding reactions, oligonucleotide ligations assays, hybridization assays, and other reactions can be used to analyze nucleic acids. In the biological field, cell-surface receptor binding assays, fluorescence-linked immunosorbent assays (FLISA), protein-protein interactions, enzyme assays, apoptosis assays, and other reactions can be used to analyze cells. These reactions have become valuable research tools with applications such as cloning, analysis of genetic expression, DNA sequencing, and drug discovery.

Recent developments in the field have led to an increased demand for biological testing devices. Biological testing devices are now being used in an increasing number of ways. It can be desirable to provide real-time detection capability in order to analyze on-going reactions.

In a real-time detection device, a plurality of lenses can be used to focus light from a light source onto the samples to be tested, and to collect the light emitted by the sample. These lenses can be bulky, taking up a considerable amount of space above the sample well tray. The use of a large number of components can make assembly and alignment of the optical components of the detection apparatus time consuming. Therefore, it can be desirable to have a simple, less complex structure.

SUMMARY

According to various embodiments, a cover for a biological sample well tray can comprise a cap for sealing a sample well. The cap can comprises a well lens for focusing light into the sample well and substantially collimating light emitted by the sample. The well can comprise a well lens for focusing light into the sample well and collecting light emitted by the sample. The well lens can be positioned in the side or bottom of the well.

According to various embodiments, a cover for a biological sample well tray can comprise a cap for sealing a sample well. The cap can comprise an elongate portion configured to permit incoming light to pass into the sample well and out of the sample well. The elongate portion can comprise a well lens for focusing light into the sample well and collecting light emitted by the sample. The elongate portion can be positioned to provide a gap between cap and sample.

According to various embodiments, a microcard for biological material. can comprise a first member and a second member. The second member can provide a plurality of sample chambers between the first member and the second member, the second member comprising a plurality of well lenses corresponding to the plurality of sample chambers. The well lenses can be in fluid contact with a sample of biological material in the sample chamber. The well lenses can focus light into the sample well and collecting light emitted by the sample.

According to various embodiments, an apparatus for a plurality of sample well strips can be provided, wherein each sample well strip comprises a plurality of sample wells defined by side walls and bottoms, and a plurality of bottom stacking projections. Each bottom stacking projection can extend downward from a sample well bottom. The bottom stacking projection can be configured to cap another sample well in another sample well strip. The side walls can comprise a plurality of well lenses for focusing light into the sample well and collecting light emitted by the sample.

According to various embodiments, a method for testing a biological sample comprises: providing a sample well or sample chamber containing said biological sample; providing a cap for the sample well, wherein the cap comprises a well lens; focusing light into the sample well; and collecting light emitted by the sample.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate several exemplary embodiments. In the drawings, According to various embodiments, FIG. 1A illustrates a cross-sectional view of a sample well of a sample well tray sealed with a transparent plastic sheet.

According to various embodiments, FIG. 1B illustrates a cross-sectional view of a sample well of a sample well tray with a flat cap.

According to various embodiments, FIG. 1C illustrates a cross-sectional view of a sample well of a sample well tray with a domed cap.

According to various embodiments.

According to various embodiments, FIG. 2A illustrates a cross-sectional view of a cap for a sample well, the cap comprising well lens.

According to various embodiments, FIG. 2B illustrates a cross-sectional view of a cap for a sample well, the cap comprising a Fresnel well lens.

According to various embodiments.

According to various embodiments.

According to various embodiments.

According to various embodiments, FIG. 6A illustrates a cross-sectional view of a cap comprising a hollow elongate portion positioned in a sample well and a separate well lens.

According to various embodiments, FIG. 6B illustrates a cross-sectional view of a cap comprising a hollow elongate portion similar to FIG. 6A.

According to various embodiments.

According to various embodiments.

According to various embodiments, FIG. 9A illustrates a cross-sectional view of a cap comprising a hollow elongated portion and a well lens.

According to various embodiments, FIG. 9B illustrates a cross-sectional view of a cap comprising a hollow elongate portion similar to FIG. 9A.

According to various embodiments, FIG. 10 illustrates a cross-sectional view of a cap comprising a solid elongate portion and a well lens.

According to various embodiments, FIG. 11A illustrates a top view of a microcard with a plurality of sample chambers comprising well lenses.

According to various embodiments, FIG. 11B illustrates a cross-sectional view of the microcard of FIG. 11A, taken along line 11B-11B of FIG. 11A, showing the microcard positioned in a horizontal orientation.

According to various embodiments, FIG. 11C illustrates a cross-sectional view of the microcard of FIG. 11A, showing the microcard positioned in a vertical orientation.

According to various embodiments.

According to various embodiments.

According to various embodiments.

According to various embodiments.

According to various embodiments.

According to various embodiments.

According to various embodiments.

According to various embodiments.

DESCRIPTION OF VARIOUS EMBODIMENTS

Figure 1D:
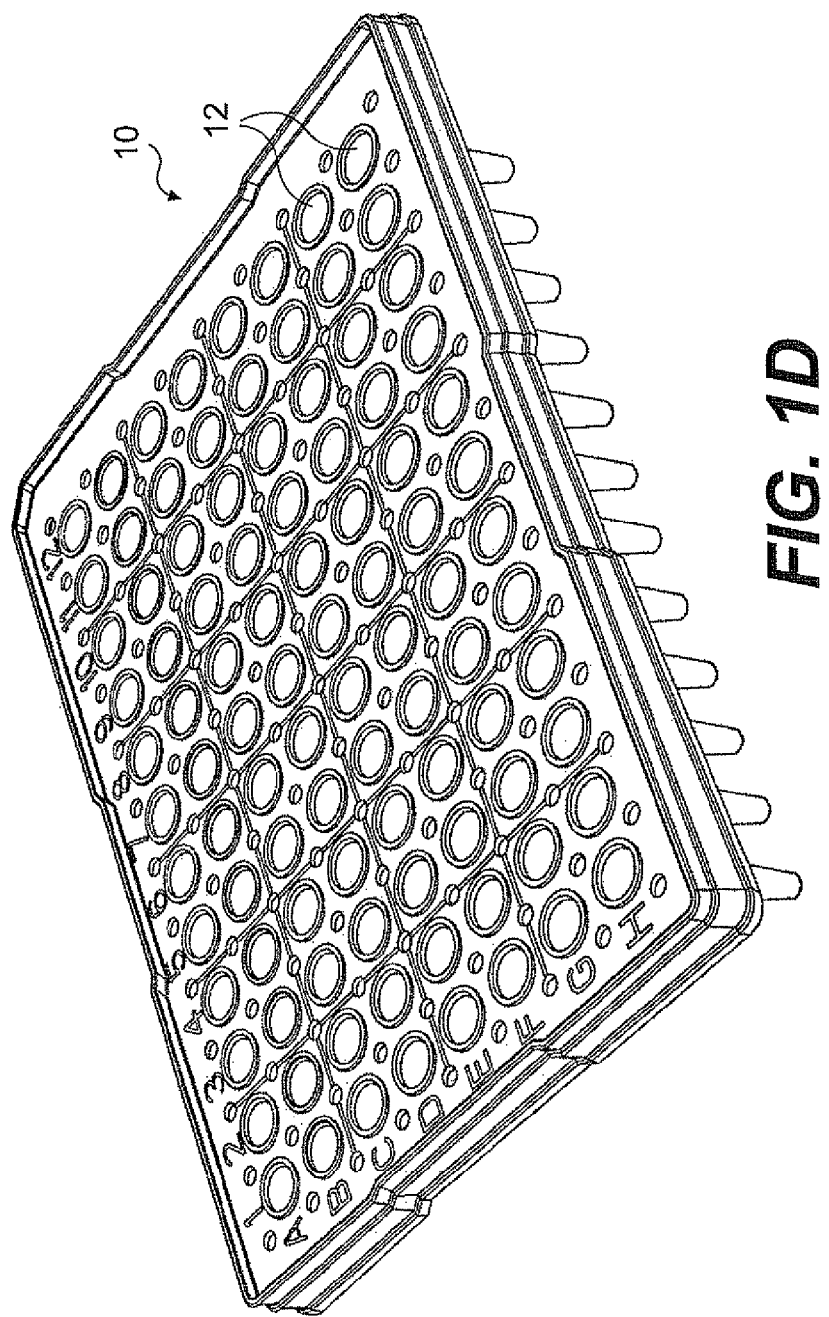
FIG. 1D illustrates a perspective view of a sample well tray with a plurality of sample wells.

Reference will now be made to various exemplary embodiments, examples of which are illustrated in the accompanying drawings. Wherever possible, the same reference numbers are used in the drawings and the description to refer to the same or like parts.

Although terms like "horizontal," "vertical," "upward," "downward," "side," "front," "upper," and "lower" are used in describing various aspects of the present teachings, it should be understood that such terms are for purposes of more easily describing the teachings, and do not limit the scope of the teachings.

According to various embodiments, a sample well tray for biological samples can be provided. An example of a sample well tray 10 with a plurality of sample wells 12 is shown in FIG. 1D. It should be understood that any type of sample well tray can be used. Sample well trays typically have a plurality of sample wells for holding a biological sample. FIG. 1A shows a sample well 12 of a sample well tray 10. A sample well tray can have a rectangular shape with a matrix of sample wells 12 contained therein. Although FIG. 1D shows a sample well tray with 96 wells in a 8×12 matrix, it should be understood that the present invention is applicable for use with sample well trays having any number of wells from one well to several thousand wells, such as, for example, 24 and 384 sample wells. Sample well trays having any number of sample well sizes can also be used. Although the term sample well tray is used, it should be understood that many aspects of the present teachings are also suitable with other substrates such as microcard sample trays, where sample wells are replaced by sample chambers.

According to various embodiments, the sample well tray can be suitable for incorporation into a number of different thermal cyclers, including but not limited to a 96-well Applied Biosystems thermal cycler. The thermal cycler can be configured for thermally cycling samples of biological material. The thermal cycling device can be configured to perform nucleic acid amplification on samples of biological material. One common method of performing nucleic acid amplification of biological samples is PCR. Various PCR methods are known in the art, as described in, for example, U.S. Pat. Nos. 5,928,907 and 6,015,674 to Woudenberg et al., the complete disclosures of which are hereby incorporated by reference for any purpose. Other methods of nucleic acid amplification include, for example, ligase chain reaction, oligonucleotide ligations assay, and hybridization assay. These and other methods are described in greater detail in U.S. Pat. Nos. 5,928,907 and 6,015,674.

According to various embodiments, the sample well tray can be used in a thermal cycling device that performs real-time detection of the nucleic acid amplification of the samples in the sample disk during thermal cycling. Real-time detection systems are known in the art, as also described in greater detail in, for example, U.S. Pat. Nos. 5,928,907 and 6,015,674 to Woudenberg et al., incorporated herein above. During real-time detection, various characteristics of the samples are detected during the thermal cycling in a manner known in the art of nucleic acid amplification. Real-time detection can permit more accurate and efficient detection and monitoring of the samples during the nucleic acid amplification process. Alternatively, the sample well tray can be used in a thermal cycling device that performs endpoint detection of the nucleic acid amplification of the samples.

According to various embodiments, the sample well tray can be configured to contact a sample block for thermally cycling the biological materials in the sample wells of the sample well tray. The sample block can be operatively connected to a temperature control unit programmed to raise and lower the temperature of the sample block according to a user-defined profile. For example, in various embodiments, a user can supply data defining time and temperature parameters of the desired PCR protocol to a control computer that causes a central processing unit (CPU) of the temperature control unit to control thermal cycling of the sample block. Several non-limiting examples of suitable temperature control units for raising and lowering the temperature of a sample block are described in U.S. Pat. No. 5,656,493 to Mullis et al. and U.S. Pat. No. 5,475,610 to Atwood et al., the disclosures of which are both hereby incorporated by reference for any purpose.

According to various embodiments, FIGS. 1A, 1B, and 1C show sealing structures for sample wells in sample well trays where the well lenses are separate. For example, FIG. 1A is a cross-sectional view of a sample well 12 of sample well tray 10 sealed with a transparent plastic sheet that can be adhesive. The sample well 12 can include side walls 14 and a bottom surface 16. The sample well 12 of FIG. 1A is configured to store a biological sample S in the interior of the side walls 14 and bottom surface 16. According to various embodiments, the sample well can have a working volume of approximately 200 µl. The volume of the sample wells can vary anywhere from 0.1 µl to thousands of microliters (µl). According to various embodiments, a volume between 5 µl and 500 µl, or 10 µl and 200 µl, or 50 µl can be used. In FIG. 1A, a thin, adhesive, transparent plastic sheet 18 is provided for sealing the top surface 20 of the sample well 12. The sheet 18 can be made out of any suitable material such as hydrocarbon-based polymers compatible with PCR as known in the art of nucleic acid amplification. These polymers can include, for example, polypropylene, polycarbonate, and polyethylene. According to various embodiments, the sheet 18 is PCR-compatible. The sheet 18 can provide an appropriate seal to the sample well 12.

According to various embodiments, as shown in FIG. 1A, a well lens 22 can be provided adjacent to the sample well 12. The well lens 22 can focus incoming light 24 from a light source (not shown) to a region in the sample of biological material S. The well lens 22 can collect the emitted light from the sample of biological material S and direct it toward the light detection apparatus (not shown). A wide variety of well lenses can be used for this purpose.

According to various embodiments, FIG. 1B shows a sample well tray 10 with a flat cap 30 placed in the sample well 12. The flat cap 30 includes a top portion 32 having a flat top surface 34 and a flat bottom surface 36. Cap 30 further includes a cylindrical sealing structure 38. According to various embodiments, the flat bottom surface 36 forms an annular surface for engaging a top surface 20 of the sample well 12. Cylindrical sealing structure 38 extends downward into the sample well 12 to engage the inside of side walls 14. The engagement of an outside surface 39 of the cylindrical sealing structure 38 serves to promote sealing of the sample well 12. The engagement of the flat bottom surface 36 of the top portion of the cap 30 with the top surface 20 of the sample well 12 also serves to promote sealing of the sample well 12. The sample well configuration of FIG. 1B further includes the well lens 22 for directing the incoming light 24 into the sample S of biological material, as discussed in greater detail with respect to FIG. 1A.

According to various embodiments, the cap 30 shown in FIG. 1B can be provided individually, in strips, or in sheets in order to facilitate the insertion and removal of the caps from the top of the sample wells 12. In a 96-well configuration, the caps 30 can be provided in strips typically having either 8 or 12 interconnected caps. In a 384-well configuration, the caps can be provided in strips typically having either 16 or 24 interconnected caps.

According to various embodiments, FIG. 1C shows sample well tray 10 with a round domed cap 40 placed in the sample well 12. The round cap 40 is similar to the flat cap 30 of FIG. 1B but has a slightly curved or domed central cap portion 42. The round cap 40 operates similarly to the flat cap. Both require the use of a separate well lens 22 positioned over the cap, for directing the incoming light 24 into the sample S of biological material. The feature of a separate well lens takes up space above the sample well tray.

According to various embodiments, a cover for a biological sample well tray is provided. In one aspect, the cover comprises a cap for sealing a sample well. The cap can comprise a well lens for focusing light into the sample well from a light source and/or collect light emitted by the sample toward a detection apparatus.

According to various embodiments, such as illustrated in FIGS. 2A and 2B, a cap with an integrated well lens is provided. As shown for example in FIG. 2A, the sample well 12 can be provided with a cap 50 having a well lens 52 integrally formed into the cap 50. The well lens 52 can provide focusing to the incoming light into the sample S of biological material, without the need for a separate well lens. This can save space, reducing costs and the number of parts and increases collection efficiency. As shown in FIG. 2A, the well lens 52 can include a top surface 54 and a bottom surface 58. The top surface 54 can be curved and the bottom surface 58 can be flat. Incoming light 24 from a light source (not shown) passes through top surface 54 through to the bottom surface 58 of the well lens 52 and into the sample well 12, focusing on a region in the sample S of biological material. The well lens 52 can further serve to collect the light emitted from the biological material and direct it toward the light detection apparatus (not shown). The term "emitted light" or grammatical variations thereof as used herein refers to the light emitted from the biological material that can include fluorescence emitted by the sample or dye molecules, for example fluorescent dyes, upon excitation by the incoming light. Emitted light can also include light scattering off of objects in the biological sample. Emitted light can also include chemiluminescence, phosphorescence, and Raman scattering. As discussed previously, the light detection can be performed either by an end-point detection apparatus or a real-time detection apparatus, depending on the specific application.

According to various embodiments, the well lens can be of any of a variety of types known in the optics. FIG. 2A shows a cap comprising a plano-convex well lens. The well lens 52 can focus substantially collimated light on an object plane within the biological sample S and collect light from an object plane in the biological sample and substantially collimate the light.

According to various embodiments, cap 50 and well lens 52 can be made out of any acceptable material, such as polypropylene and other hydrocarbon-based polymers. Other suitable materials include glass and acrylic. The material can be compatible with PCR as known in the art of nucleic acid amplification. The cap and well lens can be manufactured by any known method, such as injection or compression molding, vacuum forming, and pressure forming. In the embodiment shown, the well lens 52 is integrally formed with the cap 50. It should be understood however that the well lens 52 could be attached by any known method.

According to various embodiments, the cap can include a cylindrical sealing member configured to engage an inner surface of the sample well. As shown in FIG. 2A, cap 50 can include a sealing structure 56 integrally formed with the well lens 52 for promoting sealing of the inside of sample well 12. Sealing structure 56 is shown as a generally cylindrical member extending downward from the bottom surface 58 of the well lens 52. An outer surface 59 of the cylindrical sealing structure 56 can contact or otherwise engage the inner side wall of the sample well 12 to assist in promoting sealing of the sample well from the outside atmosphere. The outer surface 59 can be sized to have an interference fit with the inner surface of the sample well 12.

According to various embodiments, the cap 50 can further include an outer annular flat bottom surface 60 for engaging the top surface 20 of the sample well 12. This engagement also serves to promote sealing of the sample well 12.

According to various embodiments, the caps of the present teachings are suitable to fit in a wide variety of sample wells. FIG. 2A shows the cap 50 in a sample well 12 with sidewalls 14 being tapered in a conical manner. It should be understood that the sidewalls 14 of the sample wells 12 can also be non-tapered, or any other suitable configuration. Additionally, although the bottom surface 16 is shown as being rounded, the bottom surface 16 can have any other suitable configuration, such as, for example, flat. The cap can also be dimensioned to fit virtually any type of sample well. For example, with a 96-well sample well tray such as shown in FIG. 1D, the caps will be designed and sized to fit within each sample well. With a 384-well sample tray, the size of the caps will typically be smaller. It should be understood that the dimensions can greatly vary, depending on the size of the sample wells. Further, caps 50 can be manufactured into strips or sheets. The use of strips or sheets can facilitate the insertion and removal of the caps from the sample wells.

According to various embodiments, by integrating the well lens 52 into the cap 50, the need for a separate well lens spaced from the sample well 12 can be eliminated, thereby reducing the number of parts that are needed. With fewer parts, concerns about alignment between the well lens and the sample well are reduced. Moreover, integrating several parts into one can make the apparatus more compact, taking up less space.

According to various embodiments, the well lens can be a Fresnel lens integrated into the sample well cap. FIG. 2B shows an embodiment wherein the cap 70 includes a well lens 72 in the form of a Fresnel lens of the type manufactured by Fresnel Technologies of Fort Worth, Tex. FIG. 2B shows a Fresnel lens 72 integrated into a top surface 74 of the cap 70. The Fresnel lens 72 serves to focus the incoming light 24 from the light source (not shown) into the sample S of biological material. Fresnel lenses are flat on one side and on the other side comprise a plurality of ridges as shown in FIG. 2B. The angle of the ridges focuses the light even though the lens is flat. Among the characteristics of Fresnel lenses is that they can be thin and easily be made of plastic. Fresnel lenses can be used as a positive focal length collector or collimator. Fresnel lenses can have the power of convex lenses, but are thinner. This is an advantage because the optical path in the bulk of the lens is substantially reduced. Bulk transmission losses are proportional to optical path length, so reducing optical path length reduces transmission losses. The Fresnel lens 72 also serves to collect the light emitted from the sample S to be tested. The use of the Fresnel lens allows for optical detection without requiring a separate well lens.

According to various embodiments, the sample well cap is provided that includes an elongate member extending into the biological sample in the sample well. To the extent that any of the following structure is similar to the structure described above, a detailed description will not be repeated. For example, the sample well tray 10 and sample wells 12 are assumed to be identical, or at least similar in important aspects, to the sample well tray and sample well previously described. In the embodiments shown in FIGS. 3-10, a cap is provided for a sample well of a sample well tray, the cap having an elongate portion.

Figure 3:
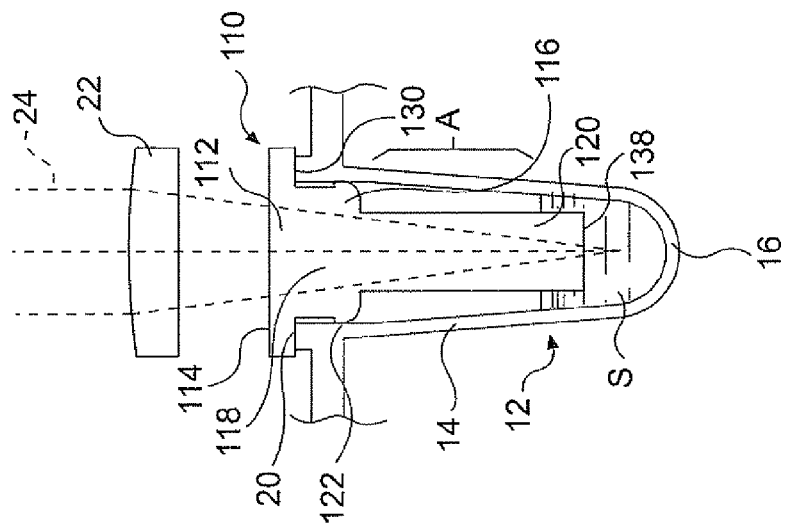
FIG. 3 illustrates a cross-sectional view of a cap comprising a solid elongate portion and a separate well lens.

According to various embodiments, the cap can be provided with an elongate member and a separate well lens. As shown for example in FIGS. 3-4, a cap 110 can be provided for the sample well 12. The cap 110 includes a top portion 112. In the embodiment shown in FIGS. 3-4, the top portion 112 comprises a flat top surface 114 and an annular bottom surface 130. The top portion 112 assists in sealing the inside of the sample wells 12 from the outside atmosphere. The top portion 112 includes an annular bottom surface 130 for engaging a top surface 20 of the sample well 12 to promote sealing of the sample well 12, as shown in FIG. 3.

According to various embodiments, the cap 110 can further comprise an intermediate portion 118 that extends from the top portion 112. In the embodiment shown, the intermediate portion 118 has a smaller diameter than the top portion 112. The intermediate portion 118 is positioned between the top portion 112 and an elongate end portion 120 of the cap 110.

In various embodiments, the intermediate portion 118 includes a generally cylindrical sealing member 116 that can be sized so that an outer surface of the intermediate portion 118 engages the inner surface of the sample well side wall 14 upon insertion in the sample well 12. The intermediate portion 118 is shown as being solid in FIGS. 3-4. The intermediate portion 118 shown in FIG. 3 includes an outer surface 122 configured for mating with the inner surface of the side wall 14. As shown in FIG. 3, the portion of the outer surface 122 that engages the inner surface of the side wall 14 has a greater diameter than the portion of the intermediate portion 118 that does not engage the side wall 14. The outer surface 122 shown in FIG. 3 provides a line contact with the sample well side wall 14 to assist in sealing the sample well 12 from the outside atmosphere. It should be understood, that alternatively, the outer surface 122 can have a constant diameter so that a large amount of the outer surface engages the inner surface of the side wall 14. In alternative embodiments, a portion of the outer surface can include a separate ring or gasket to ensure a tight seal. The engagement assists in promoting a seal between the inside of the sample well 12 and the atmosphere.

According to various embodiments, the cap 110 can further include an elongate portion 120 extending from the intermediate portion 118 of the cap. Although shown as having a different diameter than the intermediate portion 118, it should be understood that the elongate portion 120 could, in some embodiments, have the same diameter as the intermediate portion 118. Alternatively, the intermediate portion 118 can not be required, so that the elongate portion can be all that is needed. In the embodiment shown in FIGS. 3-4, the elongate portion 120 is a solid cylinder with an outside diameter less than the diameter of the intermediate portion 118. It should be understood that the elongate portion 120 can be any other suitable shape. The elongate portion 120 further includes a bottom surface 138 configured to contact the liquid sample S in the sample well.

According to various embodiments, the elongate portion 120 is configured to permit incoming light to focus in a desired portion of the sample S in the sample well 12. The incoming light can enter the cap 110 through the top surface 114 of the cap and then exit the cap 110 through the bottom surface 138 of the elongate portion 120, directly into the liquid sample. By being in direct contact with the liquid sample S in the sample well 12, condensation is prevented on the bottom surface 138 of the cap. It is desirable to avoid the formation of condensation on the bottom portion of a cap. Condensation can obstruct the optical path, thereby compromising the quality of the optical data. In various embodiments air adjacent to the caps can permit condensation to occur on the caps. In various embodiments, a heated cover raises the temperature of the caps 110 and sample well 12 to the desired temperature to avoid condensation. A heated cover, however, adds to the complexity of the device and increases costs. In various embodiments, the device can be simplified and costs can be reduced by providing the elongate portion 120 of the cap 110 that directly contacts the sample S, as described in the present teachings.

Figure 4:
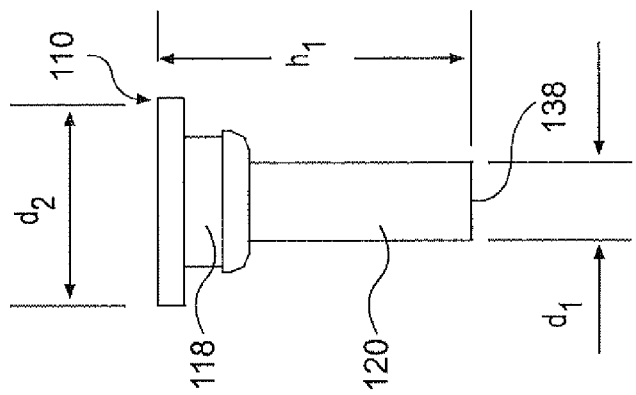
FIG. 4 illustrates a side view of the cap of FIG. 3.

According to various embodiments, as shown in FIGS. 3-4, the cap 110, including the elongate portion 120, is solid. The cap 110 can be made out of any material. According to various embodiments, the cap 110 is made out of an optically clear PCR-compatible material. Examples of suitable materials include, but are not limited to, thermoplastic materials such as polypropylene, or polycarbonate resin marketed as LEXAN® by GE Plastics, Inc. (Pittsfield, Mass.) that provides high transparency (light transmittance or clarity). Another suitable material includes resin-based polymethylpentene marketed as TPX® by Mitsui Chemicals, Inc. (Tokyo, Japan) which provides high transparency and resistance to heat and chemicals. Other high transparency plastics which can be used for the cap include polymethyl methacrylate (PMMA) marketed as Lucryl® by BASF (Germany). The cap 110, including the elongate portion 120, can be formed by any known method, such as, for example, injection molding.

It should be understood that the cap 110 described in FIGS. 3-4 is suitable for use with any type of sample well. The sample well cap can be suitably dimensioned for virtually any type of sample well and sample well tray. In one example for a 96-well tray, the cap 110 shown in FIGS. 3-4 has the following dimensions: top diameter (d2)=8.00 mm; elongate portion diameter (d1)=4.00 mm; and height (h1)=12.00 mm. These dimensions are for purposes of example only.

According to various embodiments, as shown in FIG. 3, a well lens can be provided adjacent to the cap 110. The well lens 22 can be identical to those described previously. The well lens 22 acts to direct incoming light from a light source (not shown) to a region in the sample of biological material S. The well lens 22 further serves to collect the light emitted from the biological material and direct it toward the light detection apparatus (not shown).

As discussed above, it is preferable to minimize the amount of condensation that occurs on the cap. According to various embodiments, a heater can be provided around the air gap A (see FIG. 3) above the top level of the liquid sample and below the intermediate portion 118. In various embodiments, a resistive, or other type of heater, could be provided around the sample well side walls 14 in order to heat the sample well walls and prevent condensation from occurring on the inside of the sample well where air is located. In various embodiments, the heaters can be resistive heaters or Peltier heaters used to heat a metal sample block as known in the art of thermal cycling.

Figure 5:
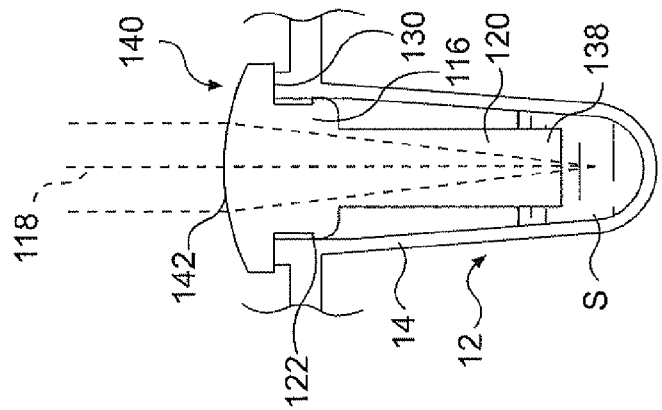
FIG. 5 illustrates a cross-sectional view of a cap comprising a solid elongate portion and a well lens.

According to various embodiments, a cap can be provided with a well lens integral with the cap, and an elongate portion extending into the sample well. FIG. 5 shows a cap 140 similar to the cap shown in FIGS. 3-4, but with a well lens 142 attached to or integral with the top portion 112 of the cap. The well lens 142 shown in FIG. 5 is a curved lens similar to those described above. In the embodiment shown in FIG. 5, the well lens 142 is integrated into the cap 140. The cap 140 can be formed in any known manner, such as injection or compression molding. The well lens 142 is configured to direct incoming light to a desired position in the interior of the sample well 12 and to direct reflected outgoing light to a detection apparatus (not shown).

According to various embodiments, by integrating the well lens 142 into the cap 140, the need for a separate well lens spaced from the sample well is eliminated, thereby reducing the number of parts that are needed. This results in the features described regarding the embodiment illustrated in FIG. 2B, such as reducing concerns about alignment, making the apparatus more compact, and reducing costs.

Figure 8:
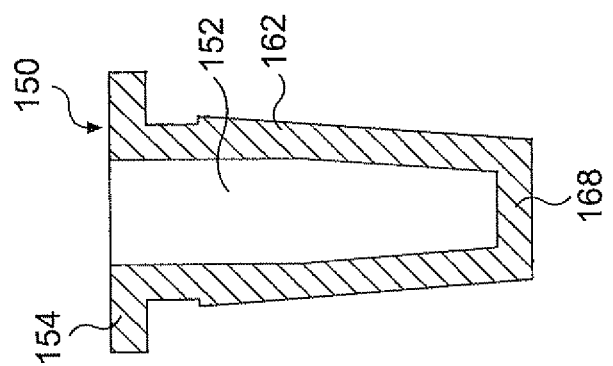
FIG. 8 illustrates a cross-sectional view of the cap comprising a hollow elongate portion of FIGS. 6A and 7.
Figure 7:
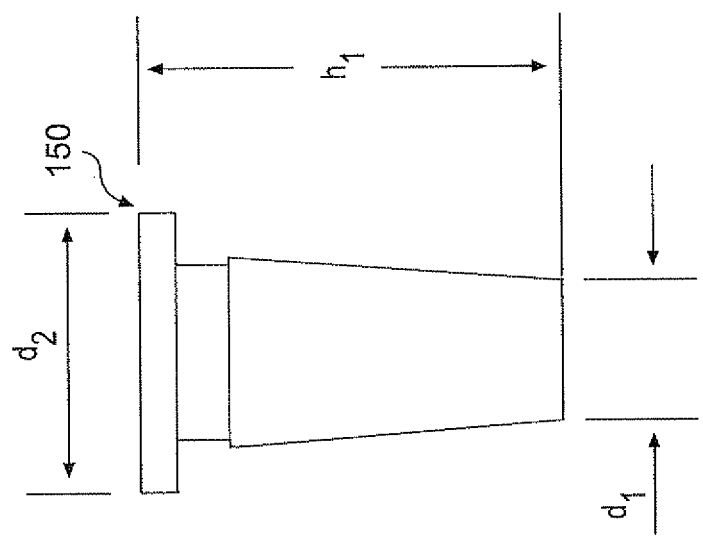
FIG. 7 illustrates a side view of the cap comprising a hollow elongate portion of FIG. 6A.

According to various embodiments, a sample well cap with a hollow elongated portion can be provided. A hollow elongate portion can have less bulk transmission loss than a solid elongate portion. As shown in FIGS. 6A, 7 and 8, a sample well cap 150 can be provided that has a hollow interior portion 152. The cap 150 includes a top portion 154 and an elongate portion 156. The top portion 154 includes an annular bottom surface 158 for engaging a top portion 20 of the sample well 12 in a manner discussed earlier.

According to various embodiments, as shown for example in FIG. 6A, the elongate portion 156 of sample well cap 150 is defined by conical walls 162 extending from the top portion 154 in a frusta-conical manner. When the cap 150 is positioned on the sample well 12, the walls taper so that a space is provided between an outer surface 164 of the conical walls 162 and an inner surface of the sample well side walls 14, except at the point of contact C between the conical walls 162 and the side walls 14. In the embodiment shown in FIG. 6A, the elongate portion 156 contacts the side walls at an upper region thereof via notch 166. As shown in FIG. 6A, the diameter of the elongated portion 156 decreases progressively as the distance from the top portion 154 increases. In various embodiments, the progression of the elongated portion decreases linearly or exponentially.

According to various embodiments, the elongate portion 156 further includes a bottom portion (or surface) 168. As shown in FIG. 6A for example, the elongate portion 156 is configured so that the bottom surface 170 of bottom portion 168 extends into and contacts the sample of biological material S to be tested. Light can pass though bottom portion 168 for purposes of optical detection. With the embodiment illustrated in FIG. 6A, the incoming light 24 from the light source (not shown) passes through the well lens 22, through the hollow interior region of the cap, and then through the bottom portion 168 into the sample S to be tested. The reflected light can then pass back through the bottom portion 168 to the well lens 22 and to the detection apparatus (not shown).

It should be understood that the cap 150 can be of any suitable dimension. In one example shown in FIG. 7, the cap has the following dimensions: top portion diameter (d2)=8.00 mm; bottom surface diameter (d1)=4.00 mm; and height (h1)=12.00 mm. This embodiment reflects a 96-well tray. The size of the cap is determined from the working volume of the sample well, and will vary depending on the desired working volume. FIG. 8 shows a cross-section of cap 150.

According to various embodiments, as shown in FIG. 6B, the cap shown in FIG. 6A can have different dimensions and a different sample well. Sample well cap 150' shown in FIG. 6B is similar to sample well cap 150 shown in FIG. 6A. In FIG. 6B, the outer surface of the upper portion 174 of the elongate portion 156' is shown as having a smooth outer surface. In contrast, the outer surface of the upper portion of the elongate portion 156 shown in FIG. 6A has a notch 166.

According to various embodiments, a sample well cap is provided with a hollow elongate portion with a bottom surface incorporating a well lens. FIG. 9A illustrates a variation of the sample well cap shown in FIGS. 6A, 7, and 8. As shown in FIG. 9A, the sample well cap 180 has a top portion and elongate portion 186 similar to that described in FIG. 6A, but further includes a well lens 182 integrally formed in a bottom surface 184 of sample well cap 180. The well lenses in this embodiment are similar to those described above. The provision of a well lens integral with the elongate portion eliminates the need for the separate well lens positioned above the sample well cap. Eliminating the need for a separate well lens has all of the advantages previously discussed.

Figure 19:
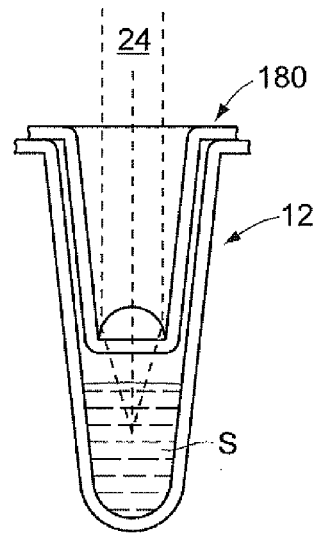
FIG. 19 illustrates a cross-sectional view of a cap comprising a hollow elongate portion similar to FIGS. 9A and 9B, providing an air gap between the bottom surface of the lens and a sample.

According to various embodiments, FIG. 9B shows a cap similar to that shown in FIG. 9A, but with different dimensions, and a different sample well. For most purposes, sample cap 180' is similar to sample cap 180 shown in FIG. 9A. According to various embodiments, as shown in FIG. 9B, the condensation cannot form on the bottom surface of the lens, because there is no air present, i.e. the bottom of the elongate portion 186 is immersed in sample S. According to various embodiments, as shown in FIG. 19, an air gap can be present between the bottom surface of the lens and sample S.

According to various embodiments, a sample well cap with an solid elongate portion and an integral well lens can be provided. FIG. 10 shows a cap with a solid elongate tube, and a sealing member surrounding the elongate tube. In the embodiment shown in FIG. 10, the cap 200 includes a sealing member 202 and an elongate tube 204. The sealing member 202 can be of any shape. In the embodiment shown in FIG. 10, the sealing member 202 is similar to the top and intermediate portions of the other embodiments. For example, sealing member 202 includes a bottom surface 206 for contacting a top surface 20 of the sample well 12, and side surfaces 208 for contacting an inner surface of the sidewall of the sample well, to promote sealing in a manner discussed previously. Sealing member 202 can be constructed of a variety of suitable materials, including hydrocarbon-based polymers compatible with PCR as known in the art of nucleic acid amplification. The sealing member 202 can include a through-hole 210 passing though the center thereof, for permitting an elongate tube 204 to be fixed thereto. In the embodiment shown in FIG. 10, the elongate tube 204 is fixedly attached to the sealing member 202, in any known manner. The elongate tube 204 can also be integral with the sealing member 202.

According to various embodiments, as shown in FIG. 10, the bottom of the elongate tube 204 can include a curved lens 210. The curved lens 210 serves to focus the incoming light from the light source (not shown) onto the sample S to be tested. The curved lens 210 is similar to those previously discussed. In one embodiment, the curved lens 210 is a spherical convex lens.

According to various embodiments, a microcard for biological material is provided. The microcard can comprise a first member, and a second member defining a plurality of sample chambers between the first member and the second member. In various embodiments, the second member can include a plurality of well lenses corresponding to the plurality of sample chambers. The well lenses are in fluid contact with a sample of biological material in the sample chamber. The well lenses focus light into the sample chamber and transmit light out of the sample chamber.

According to various embodiments, as shown in FIGS. 11A and 11B, a substrate such as microcard 250 can be provided. A microcard is a two-dimensional array of sample loci held within a continuous or non-perforated substrate. The microcard can be flexible or rigid. The substrate or microcard can contain any number of sample chambers for containing samples of biological material. The most typical number of sample chambers is 60, 96, 384, or 1536, however, the microcard can include any number of sample chambers from one to at least several thousand. FIG. 11A shows an example of a microcard 250 according to the embodiment of the present teachings.

According to various embodiments, as shown in FIG. 11B, the microcard 250 includes a first member 262 and a second member 264. In the embodiment shown in FIG. 20B, the first member 262 includes all of the features of the flow paths and sample chambers 266 in a polymeric sheet. A plurality of sample chambers 266 are defined between the first and second member.

According to various embodiments, the first member 262 can be made of any suitable material such as a polymer. One such suitable polymer is polypropylene. Other suitable polymers include, for example, polyester, polycarbonate, and polyethylene as described above. It can be desirable to make the first member 262 out of a PCR-compatible material. The second member 264 is provided as a substantially flat plate that is attached to the first member 262 to complete the formation of the features of the sample chambers and flow paths. The second member 264 can be made out of any suitable material such as a metal foil. Alternatively, the second member could be made out of any of the polymers suitable for use in the first member. The metal foil is particularly suitable because it enhances the heat transfer to the sample chambers from a sample block (not shown) that is typically positioned under the microcard. The foil backing promotes the heating of the sample S to be tested to a desired temperature. The first and second members are typically adhered to each other in order to create the requisite seal for the sample chambers.

According to various embodiments, as shown in FIG. 11B, the first member 262 includes a plurality of raised portions 268 that each define a lens 270 for light to pass through and focus on a region within the sample S to be tested. The lenses 270 are similar to those described above. In the embodiment shown, the lens 270 includes a projection 274 that extends downward into the sample to be tested. The projection is defined by an angled surface 276 and a flat bottom surface 278. The projection is preferably sized so that the bottom surface contacts the sample to be tested, as shown for example in FIG. 11B. According to various embodiments, the condensation cannot form on the bottom surface of the lens, because there is no air present.

According to various embodiments, the microcard can be positioned on a sample block for thermally cycling the biological material in the sample chambers. The sample block can be operatively connected to a temperature control unit programmed to raise and lower the temperature of the sample block according to a user defined profile. According to various embodiments, the user can supply data defining time and temperature parameters of the desired PCR protocol to a control computer that causes a central processing unit (CPU) of the temperature control unit to control thermal cycling of the sample block. Several non-limiting examples of suitable temperature control units for raising and lowering the temperature of a sample block for a microcard or other sample-holding member or other sample-holding member are described in U.S. Pat. No. 5,656,493 to Mullis et al. and U.S. Pat. No. 5,475,610 to Atwood et al., incorporated herein above. Any suitable optical detection device can also be used.

According to various embodiments, as shown in FIG. 11C, the microcard 250 can be oriented vertically. The microcard 250 is identical to the microcard shown in FIG. 11B. The lens 270 includes the projection that extends into the sample chamber to contact the sample S to be tested. This reduces the possibility of condensation on the lens 270. As shown in FIG. 11C, in the case of a vertically oriented sample card, it is preferable that the sample be of sufficient volume so that the flat surface 278 of the projection 274 is immersed in liquid. No condensation can form on the inside of the sample chamber at the flat surface 278 because it is immersed in sample S.

According to various embodiments, an apparatus including a plurality of sample well strips is provided. In various embodiments, a plurality of sample wells are defined by side walls and bottoms. The sample well strips further comprise a plurality of bottom stacking projections, each bottom stacking projection extending downward from a sample well bottom, the bottom stacking projection configured to cap another sample well in another sample well strip. The side walls can comprise a plurality of well lenses for focusing light into the sample well and collecting light emitted by the sample.

Figure 13:
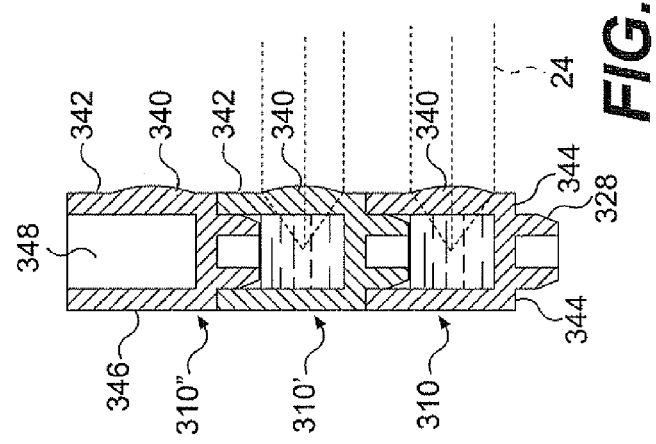
FIG. 13 illustrates a cross-sectional side view of the plurality of sample well strips of FIG. 12.
Figure 14:
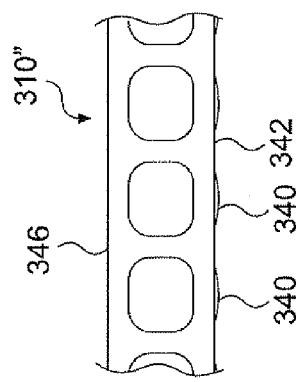
FIG. 14 illustrates a top view of the plurality of sample well strips of FIG. 12.
Figure 12:
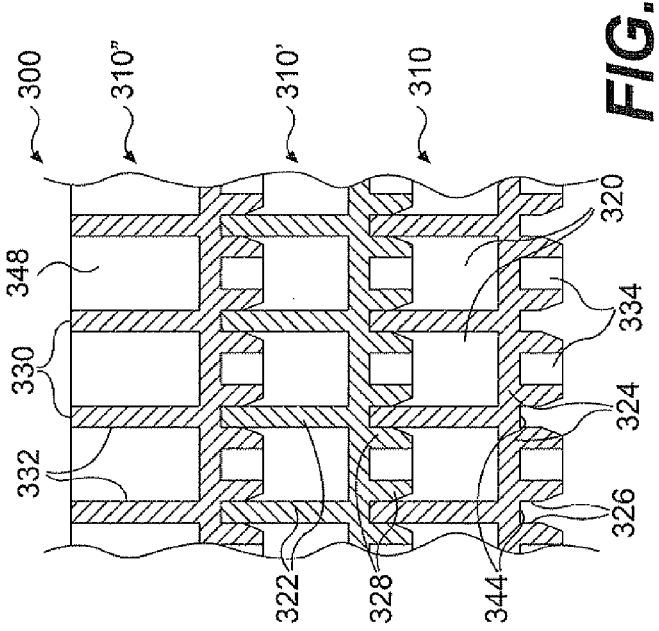
FIG. 12 illustrates a cross-sectional frontal view of a plurality of sample well strips in a stacked configuration.

According to various embodiments, as shown in FIGS. 12-14, an apparatus 300 with a plurality of sample well strips 310, 310', and 310" is provided. FIG. 12 shows three rows of sample well strips (denoted as 310, 310', and 310") stacked on top of each other, with a first row of sample well strips 310 on the bottom, a second row of sample well strips 310' in the middle, and a third row of sample well strips 310" on the top thereof. For purposes of ease of discussion, the strips will generally be referred to by reference number 310, but will be referred to as 310, 310', and 310" when necessary. It should be understood that although only three rows of sample well strips are shown in FIGS. 12-13, any suitable number of rows can be provided in accordance with the present teachings.

According to various embodiments, each of the sample well strips can comprise a plurality of sample wells 320 defined by side walls 322 and bottom surfaces 324. The strips can contain any number of sample wells. In one embodiment, each strip includes 20 wells. Other sample well strips can include anywhere from two to several hundred wells. In one embodiment, the sample wells 320 have a volume of approximately 5 μl, however, the size of the sample wells can vary from 0.001 μl to thousands of microliters (μl). In one embodiment, 48 sample well strips can be stacked, each sample well strip containing 20 wells, for a total of 960 wells. It should be understood that any number and size of sample well strips can be envisioned with the present teachings.

According to various embodiments, the side walls 332 of the sample wells 320 can be any suitable shape. According to various embodiments, as shown in FIGS. 12-14, the side walls are generally rectangular in shape, however, it is understood that the side walls can be any other shape, such as cylindrical. The side walls 322 define a top sample well opening 348 that is generally rectangular. The top surface 330 of the side walls 332 is generally flat in the example shown in FIGS. 12-14.

According to various embodiments, the sample well strips can further comprise a plurality of bottom stacking projections extending downward from a sample well bottom. As shown in FIGS. 12 and 13, a bottom stacking projection 328 extends downward from each of the sample well bottom surfaces 324. The bottom stacking projections 328 shown in FIGS. 12 and 13 are shaped to be generally rectangular in order to mate with a top sample well opening 348 of an adjacent sample well strip. According to various embodiments, there is a close interference fit between the outer surface 326 of the bottom stacking projections 328 and the inner surface 332 of the sample wells 320. According to various embodiments, the plurality of sample well strips have a snap-fit connection so that the sample well strips are securely fastened together. This close mating enhances the sealing inside of the sample wells 320. According to various embodiments, the open recess or well interior can be cylindrical to provide a maximum volume to surface area ratio.

According to various embodiments, as shown in FIGS. 12-14, the bottom stacking projection 328 includes an open recess 334. Open recess 334 provides a head space such that side walls 322 are completely in fluid contact with biological sample. The sample well bottom surfaces 324 further define a bottom recess 344 around the bottom stacking projections 328. The bottom recess 344 is a flat surface positioned between the bottom stacking projections 328. When the sample well strips 310 are stacked, the top surface 330 of the side walls 322 engages the flat surface on the bottom recess 344. As discussed previously, the bottom stacking projections 328 can be sized so that there is an interference fit in each of the sample wells when stacked. When stacked, the engagement of the top surface 330 of the side walls 322 with the bottom recess 344 further promotes sealing of the sample wells 320.

According to various embodiments, the sample well strips can include a plurality of lenses positioned in the side walls of the sample well strips. As shown in FIGS. 13 and 14, at least one lens 340 can be positioned in the side wall of each sample well 320. In the embodiment shown in FIGS. 12-14, the lens is positioned on one of the front side walls, so that an optical detection device can be placed perpendicular to a front surface 342 of the plurality of lenses. Lenses 340 are similar to those described above.

According to various embodiments, the side of the sample well strip opposite the side with the lens will be referred to as the rear surface 346, although it should be understood that terms such as "front" and "rear" are simply being used for purposes of more easily describing the teachings, and do not limit the scope of the teachings. The sample well strips include a rear surface 346. Since the optical detection is occurring through the front surface 342, in some embodiments, a heating member (not shown) such as a sample block can be positioned against the rear surface 346. This can assist in providing uniform temperatures for each of the sample wells.

According to various embodiments, the sample well strips can be stacked vertically or horizontally. FIGS. 12-14 illustrate an embodiment in which the strips are stacked vertically, therefore the stacking operation will be described for this embodiment. First, a predetermined amount of sample to be tested is inserted into the sample wells of a first sample well strip 310 by any known method, such as, for example, pipetting. Next, a second sample well strip 310' is placed above the first sample well strip 310. The second sample well strip can already be loaded with sample, or can not be loaded with sample yet. The bottom stacking projections 328 of the second sample well strip 310' are then aligned with the top openings 348 of the sample wells of the first sample well strip 310, and inserted therein. The bottom stacking projections 328 of the second sample well strip 310' should preferably snap fit or have a close interference fit with the openings of the sample wells of the first sample well strip. If the second sample well strip has not been filled with liquid sample, it can be filled with sample at this time. This process can be repeated for all of the remaining strips. It should be noted that, in the embodiment shown in FIGS. 12-14, the top or third sample well strip 310' will not typically be loaded with sample, but will instead be used as a cap for the second sample well strip 310'. In alternative embodiments, the third sample well strip 310" can be loaded with sample.

Figure 17:
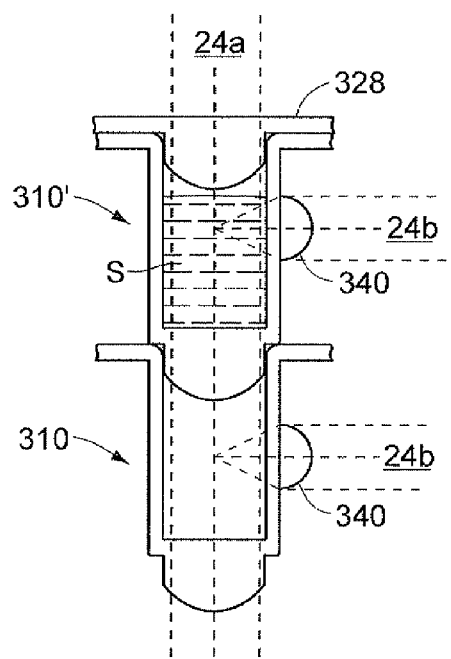
FIG. 17 illustrates a cross-sectional view of a plurality of sample well strips in a stacked configuration, with well lenses on the bottom and side, and According to various embodiments.

According to various embodiments, the sample well strips can be stacked to provide excitation light from a light source that is substantially orthogonal from the light emitted by the sample. According to various embodiments, as shown in FIG. 17, excitation light 24a passes to the sample well strips 310 and 310'. Lenses 340 can collect emitted light 24b from the sample and transmit the collected light to a detector (not shown). Excitation light 24a and emitted light 24b can be substantially orthogonal. According to various embodiments, sample well strips 310 and 310' can comprise lenses to focus excitation light 24a into a region of the sample. Lenses 340 can collect emitted light 24b from the sample and transmit the collected light to a detector.

According to various embodiments, the sample well tray can be used in a device that performs fluorescence detection. Fluorescence detection is known in the art for many applications including nucleic acids other than PCR, proteins, and cells. Fluorescent detection systems are known in the art, as also described in greater detail in, for example, U.S. Pat. No. 6,130,745 to Manian et al., incorporated herein. According to various embodiments, fluorescence detection can provide high sensitivity to detect low levels of fluorescence. According to various embodiments, fluorescence detection can provide multiplexing to detect multiple excitation and emission wavelengths in a sample.

Figure 15A:
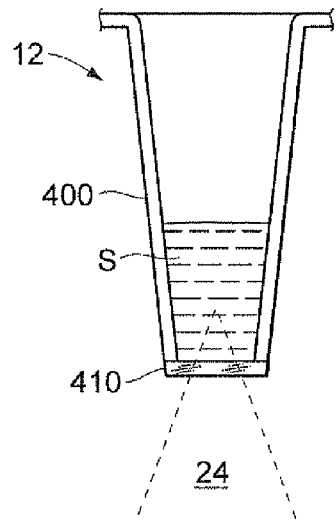
FIG. 15A illustrates a cross-sectional view of a sample well with a flat window on the bottom.
Figure 15B:
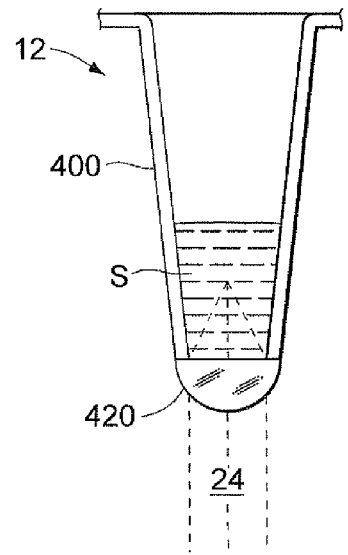
FIG. 15B illustrates a cross-sectional view of a sample well with a well lens on the bottom.
Figure 16:
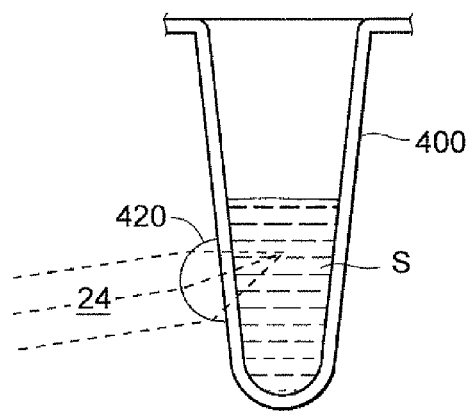
FIG. 16 illustrates a cross-sectional view of a sample well with a well lens on the side.

According to various embodiments, the well lens can be positioned at the bottom of the sample wells to focus light coming into the sample well from below the sample well tray and to collect light emitted by the sample. According to various embodiments, FIG. 15A illustrates a sample well 12 comprising a flat window 410. Window 410 is a flat surface and does not focus the light 24 emitted from the sample. According to various embodiments, FIG. 15B illustrates a sample well 12 comprising a well lens 420 for collecting light 24 emitted from sample S. Well lens 420 can focus excitation light 24 from a light source (not shown) into a region of the sample S. Well lens 420 can be a plano-convex lens. The lens radius can be chosen so that the center of curvature lies on the plano surface making the well lens aplanatic and increasing the numerical aperture of the well lens by a factor related to the index of refraction of the well lens material without introducing substantial spherical aberration, coma, or astigmatism. According to various embodiments, the apparatus can comprise an objective lens. The distance between the sample well tray and the objective lens can be decreased to compensate for the well lens. According to various embodiments, the apparatus can comprise a beam expander. A beam expander can be used with the well lens to provide substantially similar focus spot size of light as the flat window. According to various embodiments, the sides 400 of the sample well can be constructed of a dark material to reduce emitted light from escaping through sides 400. According to various embodiments, the well lens can be a Fresnel lens, or other lens known in the art of optics for focusing and collecting light. According to various embodiments, as illustrated in FIG. 16, well lens 420 can be positioned at other locations on the sample well 12, such as sides 400.

Figure 18:
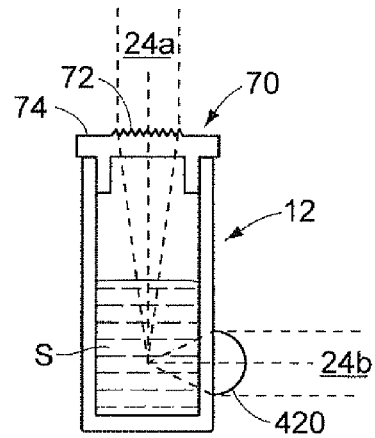
FIG. 18 illustrates a cross-sectional view of a sample well with an elongate portion leaving an air gap with sample.

According to various embodiments, the present teachings for sample wells receiving excitation light from above, sample well strips, and/or sample wells receiving excitation light from below can be combined. As shown in FIG. 18, sample well 12 can receive excitation light 24a from a light source (not shown) through cap 70 comprising a Fresnel well lens 72 integrated into the top surface 74 of cap 70. Well lens 72 can focus excitation light 24a into a region of sample S. Sample well 12 can comprise concave well lens 420 on its side. Well lens 420 can collect emitted light 24b from sample S in a direction substantially orthogonal to the direction of excitation light 24a. According to various embodiments, other combinations will be apparent to one skilled in the art.

It will be apparent to those skilled in the art that various modifications and variations can be made to the structure and methods described above. Thus, it should be understood that the present teachings are not limited to the examples discussed in the specification. Rather, the present teachings are intended to cover modifications and variations.

What is claimed is:

1. A device for holding samples of biological material, comprising:
   a sample well disposed about an axis, the sample well comprising a topmost surface, a bottommost surface, and an interior volume configured to hold at least one sample of a biological material; and
   a cap disposed during use along the axis, the cap comprising an upper portion configured during use to be disposed above the topmost surface of the sample well and an elongate lower portion configured during use to be disposed within the interior volume of the sample well, the lower portion comprising a bottommost surface;
   wherein during use the bottommost surface of the lower portion is located closer to the bottommost surface of the sample well than to the topmost surface of the sample well;
   wherein the lower portion further comprises a conical wall defining a hollow interior volume;
   wherein the bottommost surface of the lower portion forms a bottom surface of the hollow interior volume;
   wherein the cap comprises a lens located at or near the bottommost surface of the lower portion.

2. The device of claim 1, further comprising:
   a plurality of sample wells disposed about respective axes, each sample well comprising a respective topmost surface, bottommost surface, and interior volume; and
   a corresponding plurality of caps, each cap disposed during use along one of the respective axes, each cap comprising an upper portion configured during use to be disposed above the topmost surface of a respective sample well and an elongate lower portion configured during use to be disposed within the interior volume of the respective sample well.

3. The device of claim 1, wherein the lower portion comprises a characteristic outer diameter and the cap comprises a characteristic length from a top most surface of upper portion to the bottommost surface of the lower portion, the characteristic length being at least twice the value of the characteristic outer diameter.

4. A system for analyzing samples of biological material, comprising:
   a sample well disposed about an axis, the sample well comprising a topmost surface, a bottommost surface, and an interior volume configured to hold at least one sample of a biological material;
   a cap disposed along the axis, the cap comprising an upper portion disposed above the topmost surface of the sample well and an elongate lower portion disposed within the interior volume of the sample well, the lower portion comprising a bottommost surface, the bottommost surface of the lower portion being located closer to the bottommost surface of the sample well than to the topmost surface of the sample well;
   wherein the lower portion further comprises a conical wall defining a hollow interior volume;
   wherein the bottommost surface of the lower portion forms a bottom surface of the hollow interior volume;
   wherein the cap comprises a lens located at or near the bottommost surface of the lower portion.

5. The system of claim 4, further comprising:
   a light source configured to provide excitation light to the sample well; and
   a detection system configured to receive fluorescent light from the sample.

6. The system of claim 4, further comprising:
a thermal cycler configured to configured to perform nucleic acid amplification on a sample of biological material.

7. The system of claim 4, further comprising:
a plurality of sample wells disposed about respective axes, each sample well comprising a respective topmost surface, bottommost surface, and interior volume; and
a corresponding plurality of caps, each cap disposed along one of the respective axes, each cap comprising an upper portion disposed above the topmost surface of the respective sample well and an elongate lower portion disposed within the interior volume of the respective sample well.

8. The system of claim 4, wherein the lower portion comprises a characteristic outer diameter and the cap comprises a characteristic length from the upper portion to the bottommost surface of the cap, the characteristic length being at least twice the value of the diameter.

\* \* \* \* \*